United States Patent
Xue et al.

(10) Patent No.: US 10,687,726 B2
(45) Date of Patent: Jun. 23, 2020

(54) SYSTEM AND METHOD FOR PROCESSING ECG RECORDINGS FROM MULTIPLE PATIENTS

(71) Applicant: General Electric Company, Schenectady, NY (US)

(72) Inventors: Joel Q. Xue, Wauwatosa, WI (US); Mark Gilbert Langer, Wauwatosa, WI (US)

(73) Assignee: General Electric Company, Schenectady, NY (US)

( * ) Notice: Subject to any disclaimer, the term of this patent is extended or adjusted under 35 U.S.C. 154(b) by 212 days.

(21) Appl. No.: 15/806,009

(22) Filed: Nov. 7, 2017

(65) Prior Publication Data
US 2019/0133483 A1   May 9, 2019

(51) Int. Cl.
*A61B 5/04*  (2006.01)
*A61B 5/0428*  (2006.01)
(Continued)

(52) U.S. Cl.
CPC .......... *A61B 5/04288* (2013.01); *A61B 5/046* (2013.01); *A61B 5/0432* (2013.01);
(Continued)

(58) Field of Classification Search
CPC . A61B 5/04288; A61B 5/0432; A61B 5/7203; A61B 5/7221; A61B 5/0472;
(Continued)

(56) References Cited

U.S. PATENT DOCUMENTS 6,304,772 B1   10/2001 Taha et al.
6,304,773 B1   10/2001 Taylor et al.
(Continued)

FOREIGN PATENT DOCUMENTS

CN   104382590   3/2015
CN   104473629   4/2015
(Continued)

OTHER PUBLICATIONS

GE Healthcare, "GE EK-Pro Arrhythmia Algorithm", DOC0783131, 2010 General Electric Company.

*Primary Examiner* — Amanda K Hulbert
*Assistant Examiner* — Natasha Patel
(74) *Attorney, Agent, or Firm* — Andrus Intellectual Property Law, LLP

(57) ABSTRACT

A system for processing ECG recordings from multiple patients includes a preprocessing database containing unprocessed ECG records from multiple patients, a reporting database containing processed ECG records from multiple patients, a processor, and a triage module executable on the processor to assess each of the unprocessed ECG recordings from the multiple patients. The triage module is executable to detect a presence or absence of one or more known abnormalities and determines at least one abnormality identifier based on the detected known abnormality. One or more abnormality groups are then identified based on the abnormality identifiers. A normal group of ECG recordings from multiple patients is then identified from those ECG recordings that are not in the abnormality group. The normal group of ECG recordings is then stored in the reporting database then associated a normal identifier.

20 Claims, 8 Drawing Sheets

(51) Int. Cl.
*A61B 5/00* (2006.01)
*A61B 5/0432* (2006.01)
*G16H 50/20* (2018.01)
*A61B 5/046* (2006.01)
*A61B 5/0472* (2006.01)
*G16H 15/00* (2018.01)
*G16H 10/60* (2018.01)

(52) U.S. Cl.
CPC ........... *A61B 5/7203* (2013.01); *G16H 50/20* (2018.01); *A61B 5/04012* (2013.01); *A61B 5/0472* (2013.01); *A61B 5/7221* (2013.01); *G16H 10/60* (2018.01); *G16H 15/00* (2018.01)

(58) Field of Classification Search
CPC .... A61B 5/04012; A61B 5/046; G16H 10/60; G16H 15/00; G16H 50/20
USPC ........................................................ 600/522
See application file for complete search history.

(56) References Cited

U.S. PATENT DOCUMENTS

| | | |
|---|---|---|
| 6,490,479 B2 | 12/2002 | Bock |
| 6,507,753 B1 | 1/2003 | Xue et al. |
| 6,687,685 B1 | 2/2004 | Sadeghi et al. |
| 7,469,287 B1 | 12/2008 | Castillo et al. |
| 7,702,382 B2 | 4/2010 | Xue et al. |
| 7,792,573 B2 | 9/2010 | McDougall et al. |
| 8,352,018 B2 | 1/2013 | Xue et al. |
| 9,078,572 B2 | 7/2015 | Brodnick |
| 9,131,843 B2 | 9/2015 | Myr |
| 9,254,092 B2 | 2/2016 | Albert et al. |
| 9,351,652 B2 | 5/2016 | Dziubinski et al. |
| 2006/0079795 A1 | 4/2006 | Busche |
| 2007/0027630 A1 | 2/2007 | Sanchez |
| 2011/0129129 A1* | 6/2011 | Avinash ................... A61B 5/04 382/128 |
| 2012/0123232 A1* | 5/2012 | Najarian ............... A61B 5/0022 600/345 |
| 2013/0006131 A1* | 1/2013 | Narayan ................ A61B 5/042 600/508 |
| 2013/0085405 A1 | 4/2013 | Bera |
| 2017/0105683 A1 | 4/2017 | Xue |

FOREIGN PATENT DOCUMENTS

| | | |
|---|---|---|
| CN | 104783782 | 7/2015 |
| EP | 1179319 | 2/2002 |
| JP | 4841028 | 4/2001 |

* cited by examiner

| Beat module (HMM output, 5 secs) | Beat AFIB value |
|---|---|
| Chaotic | 1 |
| Organized | 0 |
| Chaotic | 1 |
| Chaotic | 1 |
| Chaotic | 1 |
| ... | ... |

| Segment module (5 second output) | Segment AFIB value | Noise level |
|---|---|---|
| Afib | 1 | – |
| NSR | 0 | – |
| Afib | 0 | – |
| Afib | 0 | + |
| Afib | 1 | – |
| ... | ... | ... |

| AFIB detect module | | | | CL % |
|---|---|---|---|---|
| Hi-Sens | Bal. | Hi-Spec | | |
| 1 | 1 | 1 | | CL |
| 0 | 0 | 0 | | CL |
| 1 | 1 | 0 | | CL |
| 1 | 1 | 0 | | CL-20% |
| 1 | 1 | 1 | | CL |
| ... | ... | ... | | CL |

FIG. 7

SYSTEM AND METHOD FOR PROCESSING ECG RECORDINGS FROM MULTIPLE PATIENTS

BACKGROUND

Detection and/or monitoring of certain cardiac disorders and diseases require long term intermittent ECG monitoring. Irregular heart beat, for example, is a group of disorders that are often not persistent or chronic, and thus often not present when a resting 12-lead ECG is obtained. This has prompted the development of easy-to-use long-term ECG recording devices, which typically rely on a single lead ECG or a small number of leads. These include electrode patches that can be continuously worn for weeks at a time or simple hand-held ECG devices that can be used by the patient to periodically (yet regularly) capture 30 seconds of ECG data.

Atrial fibrillation ("AFIB") is the most common form of an irregular heartbeat. In AFIB, the heart's atrial walls do not produce an organized contraction and instead quiver. Thus, no organized heart beat rhythm can be detected from a patient experiencing AFIB. This arrhythmia puts patients at significant risk because it allows blood to pool and stagnate in the left atrium and, thus, form a clot. This clot can slough off and travel up to the brain where it can block sufficient blood flow to a portion of the brain where upon it will begin to die, thus causing a stroke. AFIB causes up to a quarter of all strokes and is often undetected until a stroke occurs. It is estimated that approximately a third of AFIB is asymptomatic. The prevalence of AFIB is high and age dependent, from 0.7% in the ages 55-59 to 17.8% for 85 years or older. Yet, AFIB is notoriously hard to detect.

Intermittent AFIB has been found to increase the risk of stroke, although perhaps to a lesser degree than persistent AFIB. Moreover, it has been found that a significant portion of those who suffer from transient ischemic attacks or cryptogenic strokes have intermittent AFIB. Thus, there is increased interest in recording transient episodes of AFIB which requires something other than the use of a diagnostic resting ECG device. However, detecting AFIB in an ECG recording poses challenges.

The most common method for automatically detecting AFIB in ECG recordings relies heavily on the fact that AFIB is a chaotic atrial arrhythmia, randomly conducted to the ventricles. As such, the time periods between features of the QRS waves, as measured by the RR intervals, should be continuously varying in the presence of AFIB. It is this attribute of AFIB, that it is a continuously chaotic rhythm, that is used by most ambulatory ECG analysis programs to detect AFIB. However, RR intervals of normally conducted beats can vary for other types of benign arrhythmias that are not AFIB. Examples include premature atrial complexes (PACs) or sinus arrhythmia (SA), which are both quite common in the normal population. While these benign arrhythmias do exhibit as variability in RR intervals, these arrhythmias are not actually continuously chaotic or random. Differentiating between benign arrhythmias and AFIB requires specialized training and is time consuming.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

A system for processing ECG recordings from multiple patients includes a preprocessing database containing unprocessed ECG records from multiple patients, a reporting database containing processed ECG records from multiple patients, a processor, and a triage module executable on the processor to assess each of the unprocessed ECG recordings from the multiple patients. The triage module is executable to detect a presence or absence of one or more known abnormalities and determines at least one abnormality identifier based on the detected known abnormality. One or more abnormality groups are then identified based on the abnormality identifiers. A normal group of ECG recordings from multiple patients is then identified from those ECG recordings that are not in the abnormality group. The normal group of ECG recordings is then stored in the reporting database then associated a normal identifier.

A method of processing ECG recordings from multiple patients includes receiving a batch of ECG recordings from multiple patients wherein each ECG recording is a time series of ECG data recorded from a patient, and assessed to detect the presence or absence of one or more known abnormalities, and an abnormality identifier is then determined based on the detected known abnormality. One or more abnormality groups are then identified within the batch of ECG recordings based on the abnormality identifiers. A normal group of ECG recordings is identified within the batch of ECG recordings that are not in the one or more abnormality groups. Each ECG recording in the normal group is then stored in a database in conjunction with the normal identifier.

BRIEF DESCRIPTION OF THE DRAWINGS

The present disclosure is described with reference to the following Figures.

FIG. 7 provides tables depicting exemplary logic that may be utilized as part of a method of processing ECG data to detect atrial fibrillation according to the present disclosure.

DETAILED DESCRIPTION

Figure 1:
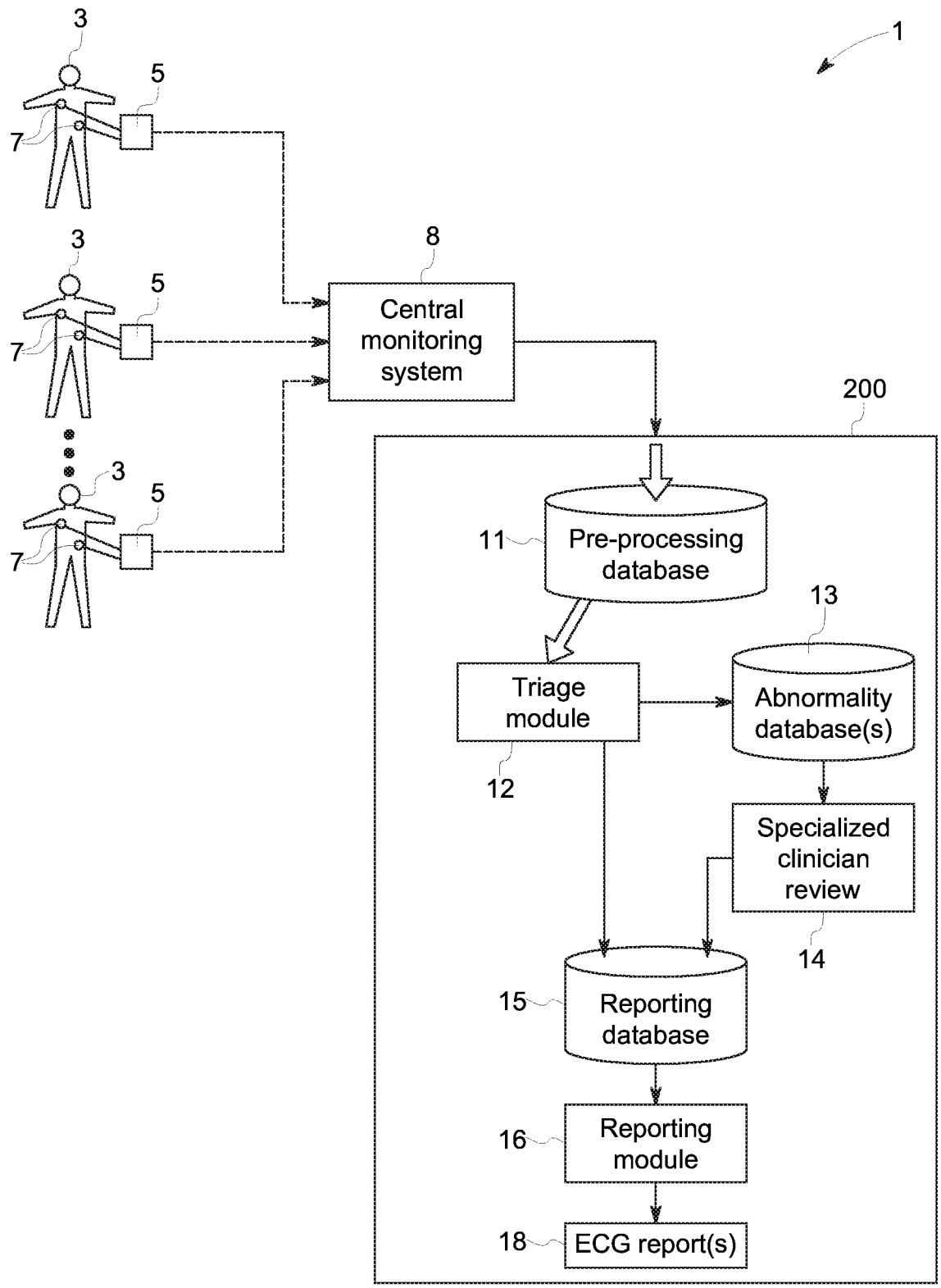
FIG. 1 schematically depicts one embodiment of a system for processing ECG recordings from multiple patients.

Independent Diagnostic Testing Facilities (IDTFs) are often challenged with receiving and processing the massive amounts of ECG data recorded by these long-term ECG recording devices that monitor a patient for weeks or months at a time. IDTFs are tasked with viewing and editing thousands of ECG recordings per day. Furthermore, the amount of time and expertise necessary to evaluate each of these tracings is not the same. Some may require a specialized clinician with training and expertise in detection of certain abnormalities (e.g., AFIB) and take minutes to evaluate; others are relatively simple and can be reviewed by a novice clinician in only a few seconds. This is often due to the following factors: (1) poor signal quality and/or high levels of noise; (2) the duration of the arrhythmic event; and (3) the degree of complexity of the arrhythmic event. Due to these reasons, laboratory services often use manual methods to triage the reading of recordings, such as to allocate them to different staff members that have different skill sets. These manual methods require significant manpower and time, which raises the price of lab services and the delay in providing results.

In view of the recognition of the forgoing problems and challenges faced in the review of massive amounts of ECG recordings from long-term ECG recording devices, the inventors developed the present system and method for triaging sets, or batches, of ECG recordings from multiple patients. The disclosed system and method for processing ECG recordings from multiple patients divides the ECG recordings into a noise group, a normal group, and one or more abnormality groups. Here, "normal" is used to refer to a recording where no abnormality is detected, and thus "normal" is a relative term since the detection might not cover all ECG abnormalities. An additional group of conditions based on several ECG parameters are used to increase the accuracy of the interpretation of an ECG as normal. The abnormality groups are then directed for specialized clinician review based on the detected abnormality. In certain embodiments, the normal group may be stored directly in the reporting database and may bypass the one or more clinician review stages, thereby saving significant review time by clinicians, which ultimately speeds up and reduces the cost of IDTF services. In certain embodiments, a triage module, which is a software module configured to conduct an initial assessment of the unprocessed ECG recordings from multiple patients in order to triage and group the ECG recordings as described above. In certain embodiments the triage module may be configured to operate in multiple different modes that adjust the sensitivity/specificity of the algorithm for grouping the ECG recordings, such as for detecting one or more known abnormalities in a respective ECG recording.

The inventors recognized a need for a robust and reliable system and method for automatically detecting AFIB that can process any ECG data—e.g., regardless of signal source, lead arrangement or number of leads, sample frequency, data resolution, noise level, etc.—to facilitate triaging the thousands of ECG recordings received by an IDTF daily.

FIG. 1 depicts one embodiment of a system 1 for processing ECG recordings 10 from multiple patients 3. In the figure, multiple ECG monitors 5 record time series ECG data from patients 3. In the depicted embodiment, each ECG monitor 5 is receiving potentials from two electrodes 7 attached to the respective patient 3. Thus, one lead of ECG data is recorded by each ECG monitor 5, which may be recorded over a very long period of time, such as days, weeks, or months. As described above, the ECG data may be recorded in intervals, such as intervals of thirty seconds or as long as several minutes. Alternatively, the ECG monitor 5 may be configured to continually record ECG data from the patient. The ECG recordings 10 are then transmitted or transferred to the central monitoring system 8 for storage and communication to a central processing facility, such as by an IDTF. For example, the central monitoring system 8 may be a network that receives and aggregates transmissions from a multitude of ECG monitors 5, which may be affiliated with a medical provider or with and IDTF. In other embodiments, the central monitoring system 8 may be eliminated and the ECG monitors 5 may communicate directly with the computing system 200 of the central processing facility. Transmissions between the patient monitors 5 and the central monitoring system 8 and/or between the central monitoring system 8 and the central processing facility may be by any data transmission means and/or protocol, which preferably are sufficiently secure to protect patient confidentiality.

Upon receipt at the computing system 200 of the central processing facility, the batch or group of ECG recordings 10 from the multiple patients 3 may be stored in a pre-processing database 11 containing ECG recordings awaiting triage processing. The computing system 200 at the central processing facility, such as an IDTF, include a pre-processing database containing unprocessed ECG recordings from the multiple patients 3, and a triage module 12 that processes the ECG recordings 10 from the pre-processing database and sorts them into groups of ECG recordings, and directs those groups to further storage locations or systems, such as the abnormality database 13 and the reporting database 15. The triage module 12 may be comprised of several different sub-modules containing computer executable instructions for detecting and analyzing noise level, detecting a presence or absence of one or more known abnormalities, and/or detecting whether a normal sinus rhythm is present in each respective ECG recording 10. For example, the triage module 12 may include a noise analytic module 21, an abnormality detection module 23, and a normal detection module 25. Moreover, each of those modules 21 through 25 may include further submodules containing computer executable instructions for carrying out various tasks. For example, the abnormality detection module 23 may include various sub-modules for detection of particular types of abnormalities. Highlighting just one example described in detail herein, the abnormality detection module 23 may include on or more submodules for detection of AFIB within an ECG recording 10.

The noise analytic module 21 may be configured to determine a noise level for each of the ECG recordings from the multiple patients and identify a noise group of ECG recordings from the multiple patients as those ECG recordings 10 having a noise level above a threshold noise level. For example, the noise level may be a signal-to-noise ratio, which is then compared to one or more corresponding signal-to-noise thresholds for determining whether an ECG recording 10 can provide sufficiently reliable information regarding the patient's actual cardiac rhythm. For example, the noise level may be placed on a noise scale, or may otherwise be indicated by assigning any one of three or more values. In other embodiments, the noise level may incorporate or include a reliability threshold determination, such as a positive value if the noise exceeds a noise threshold and a negative value (or a zero) if the noise does not exceed a threshold.

Figure 2:
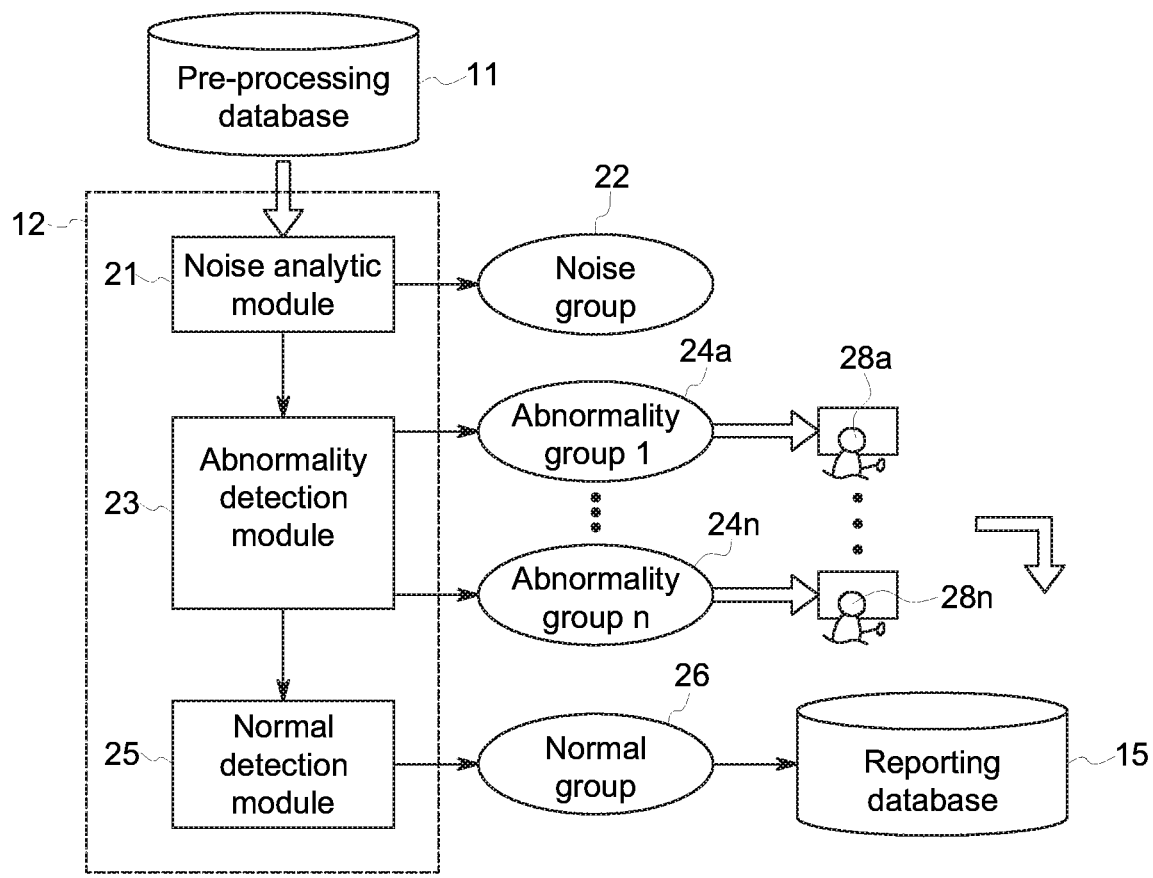
FIG. 2 schematically depicts on embodiment of a method for processing ECG recordings from multiple patients.

In the embodiment of FIG. 2, the noise analytic module 21 isolates those ECG recordings 10 from a batch of ECG recordings from multiple patients 3 that are too noisy to provide reliable information about the respective patient's physiology by grouping those recordings into a noise group 22. Those ECG recordings 10 and the noise group 22 may then be removed from the larger group requiring assessment, such as for determination of whether the ECG recording represents an abnormality or a normal sinus rhythm. For example, those ECG recordings 10 and the noise group 22 may each be associated with a noise designator indicating to the system 1 and/or to any reviewing clinician that the recording is noisy and should be generally ignored. The noise group 22 of ECG recordings 10 may be stored in a separate database, or may be maintained with the other ECG recordings, such as in the reporting database 15, and maintained with the associated noise indicating their group status.

The ECG recordings 10 that are not in the noise group 22 may be reviewed within the triage module 12 according to logic for detecting the presence or absence of one or more known abnormalities. For example, logic may be included to identify various abnormalities, such as atrial fibrillation, artificial pacing, ectopic atrial rhythm, atrial flutter, junctional rhythm, premature atrial contractions (PACs), or others. Similarly, logic may be included to detect the presence of sinus elements that may rule out certain or all abnormalities, including the presence of a p-wave or a normal sinus rhythm, such as an assessment with respect to a group of key ECG parameters an corresponding normal ranges. Such key parameters may include, for example, heart rate, PR interval, QRS duration, QT/QTc intervals (wherein QTc is heart rate corrected QT interval), and/or others. The inventors have recognized that such an abnormality check relying on key parameters can be especially appropriate for interpreting ECG recordings involving relatively few input leads (such as 3 leads) and where the signal-to-noise ratio is relatively low compared to a clinically-administered ECG recording—factors which are common with long-term ECG recordings. However, in other embodiments, the triage module 12 may be configured to make a more exhaustive, traditional diagnostic ECG assessment.

The abnormality detection module 23 may include logic to detect numerous different abnormalities and to assign an abnormality identifier 36 accordingly. To provide just one example, upon recognizing features consistent with premature atrial contractions, the abnormality detection module 23 may assign a PAC identifier to the respective ECG recording 10. That ECG recording 10 may then be assigned to an abnormality group 24 accordingly, such as to a PAC abnormality group comprising ECG recordings 10 with PAC abnormality identifiers. Likewise, the abnormality detection module 23 may further include logic for detecting the presence of atrial fibrillation and signing an AFIB identifier and creating an AFIB abnormality group to isolate those ECG recordings 10 where atrial fibrillation appears to be present.

The ECG recordings 10 in each abnormality group 24a-24n are directed for review by a respective specialized clinician 28a-28n. As such, the abnormality groups 24a-24n may be stored in one or more abnormality databases 13. For example, each abnormality group 24a-24n may be stored in a dedicated abnormality database 13 from which the respective specialized clinician 28a-28n may fetch the ECG recordings 10 therefrom. Alternatively, multiple or all abnormality groups 24a-24n may be stored in a single abnormality database 13, and the specialize clinicians 28a-28n may locate the ECG recordings 10 from the respective abnormality group 24a-24n based on the abnormality identifiers.

The triage module 12 may further be configured to identify a normal group 26 containing ECG recordings 10 from the multiple patients 2 that exhibit a normal sinus rhythm, and/or exhibit normal ranges for key ECG parameters, like a normal PR interval, QRS duration, and QT/QTc. For example, the normal ECG recordings may be isolated from those ECG recordings 10 that are not in the noise group 22 or in the one or more abnormality groups 24a through 24n. In certain embodiments, a normal detection module 25 may assess those recordings where no abnormality was detected to determine whether a normal sinus rhythm is dominant, or likely dominant, in the respective ECG recording 10. In certain embodiments, where a sinus rhythm is detected in the abnormality detection module 23, such ECG recording 10 may be further assessed (either by the abnormality detection module 23 or the normal detection module 25) to determine whether a normal sinus rhythm is dominant within the ECG recording. For example, a beat-by-beat assessment of the respective ECG recording may be made to determine whether the normal sinus rhythm is detected more often than not, or at least a threshold percentage of the beats in the ECG recording 10.

In certain embodiments, the normal detection module 25 may calculate a normal confidence level for each ECG recording in the normal group, and those ECG recordings 10 having at least a threshold normal confidence level may be stored directly into the reporting database 15 and may bypass the clinician review process. The confidence level is determined based on the ratio of normal ECG called from multiple segment analysis, noise level, etc. For example, if 9 out of 10 ECG segment analysis are called normal and the noise level is low, then the confidence level is very high. On the other hand, if only 4 out of 10 segment analyses are called normal, or most ECG segments are very noisy, then the confidence level is low. Those ECG recordings 10 having a normal confidence level that is below the threshold normal confidence level may then be directed to a clinician for review accordingly. For example, each ECG recording 10 assigned to the normal group 26 may receive a normal identifier 40 and normal confidence level 41 may be associated with the ECG recording 10. The reviewing clinician may then see the normal identifier 40 and normal confidence level 41, which provides information that can be utilized to reduce the review time. Moreover, the ECG recordings 10 may be directed accordingly.

In certain embodiments, the noise level logic may be incorporated into one or more other modules, such as the abnormality detection module 23 and/or the normal detection module 25, or may be otherwise incorporated into other signal processing tasks rather than as an initial determination and initial isolation of a noise group. In certain embodiments, the excessively noisy ECG recordings may be filtered out by the abnormality detection module 23 and/or the normal detection module 25 such that they are not included in either the normal group 26 or the one or more abnormality groups 24a-24n. Thus, the noise group 22 may not be formed as an initial processing task (or perhaps not formed at all). For example, the noise level may be accounted for in the confidence level calculation for the normal or abnormal classifications. Those and other examples of such embodiments are described hereinbelow.

Figure 4:
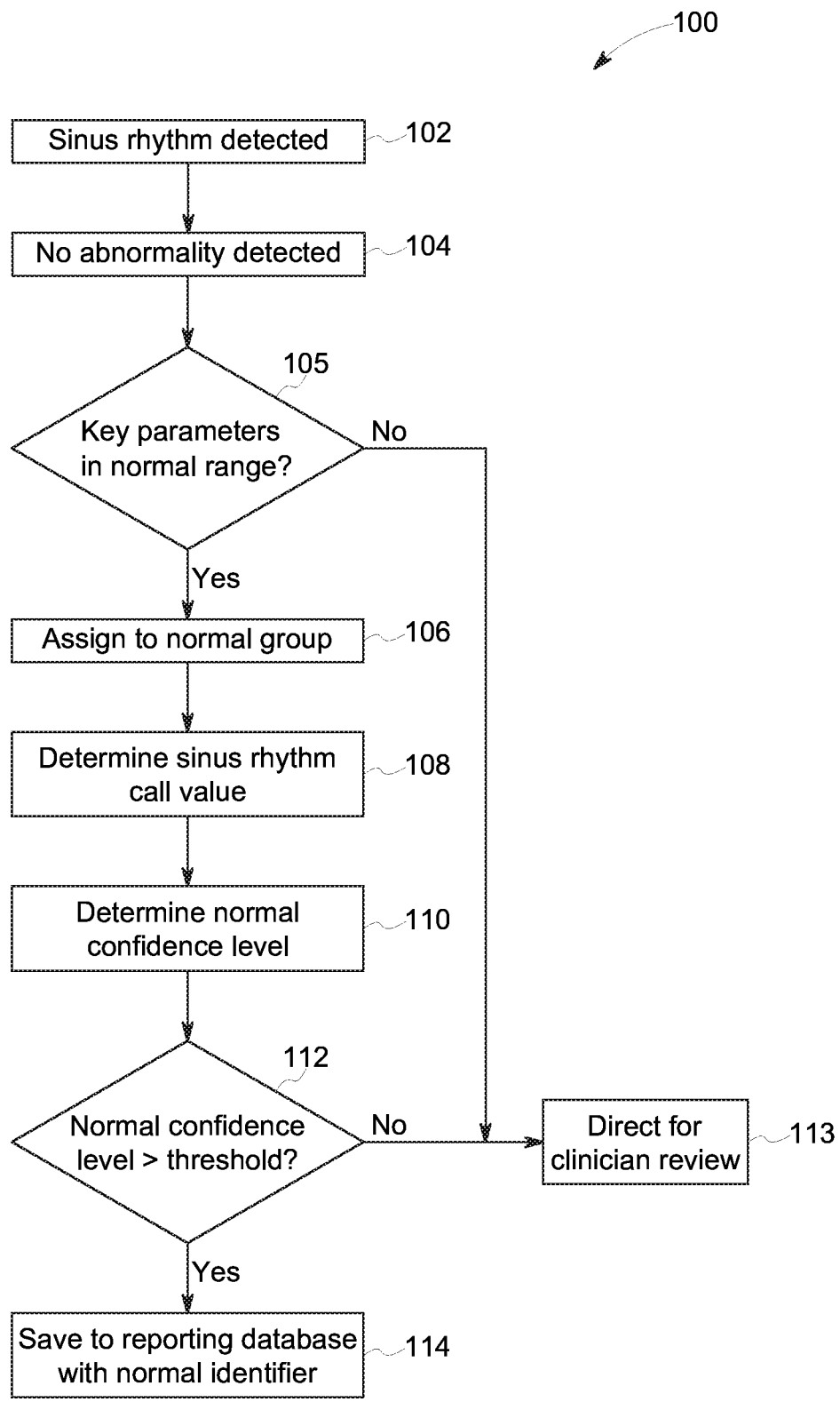
FIGS. 4-6 depict embodiments of methods, or portions thereof, for processing ECG recordings from multiple patients.

FIG. 4 depicts one embodiment of a method of processing ECG waveforms for multiple patients and, more specifically, a portion thereof relating to identifying a normal group of ECG recordings 10 and routing the normal ECG recordings to the reporting database 15 or to a clinician for review. At step 102 a sinus rhythm is detected in the time series of ECG data and an ECG recording 10. The sinus rhythm detection may occur, for example, as part of the abnormality detection process executed by instructions within the abnormality detection module 23, and/or may occur by executing the instructions within the normal detection module 25. For example, detection of a sinus rhythm may occur at steps executed to rule out the possibility of AFIB or other abnormalities where an irregular heartbeat is present.

If a sinus rhythm is detected at step 102 and no abnormality is detected at step 104, then step 105 may be executed to assess whether the respective time series of ECG data exhibits key parameters that fall within a normal range, such as a normal heart rate, PR interval, QRS duration, and QT/QTc intervals. If all key ECG parameters are not within the normal range at step 105, then the ECG recording 10 is directed for clinician review (represented at step 113).

Assuming that the key ECG parameters are in normal range at step 103, the ECG recording 10 may be assigned to the normal group 26 at step 106. In certain embodiments, the normal group may be further refined by further assessing to determine that a normal sinus rhythm is dominant in the respective ECG recording 10 and/or that excessive noise is not present (especially if the noise group is not separated out at an earlier stage). For example, instructions may be executed at step 108 to determine a sinus rhythm call value indicating the percentage or number of sinus rhythm calls within the ECG recording 10. A normal confidence level 41 is determined at step 110 based, at least in part, on the sinus rhythm call value. The normal confidence level 41 represents the likelihood that a normal sinus rhythm is dominant in the respective ECG recording 10. For example, a sinus rhythm call value indicating that a normal sinus rhythm was detected in a high percentage of the heartbeats within the ECG recording would translate into a high normal confidence level 41. Conversely, a low sinus rhythm call value where a normal sinus rhythm was detected in only a small percentage of the ECG recordings would translate into a low normal confidence level 41.

Other aspects of the recording may be accounted for in the normal confidence level 41, such as the noise level. In certain embodiments, the normal confidence level 41 may be reduced based on the detection of noise. For example, the confidence level reduction may be a sliding scale based on the noise level, where the higher the noise level the greater the reduction in confidence level.

The normal confidence level 41 for a particular ECG recording is compared to a normal confidence level threshold at step 112. If the normal confidence level 41 does not exceed the threshold, then the ECG recording 10 is directed for clinician review at step 113. If the normal confidence level does exceed the threshold, then it may be directed to the reporting database 15 at step 114, where it is saved in preparation for inclusion in an ECG report 18 for review by the ordering physician and/or inclusion in the patient's medical record. Thus, those ECG recordings 10 having a normal confidence level 41 that exceeds the threshold are automatically reported and bypass the need for clinician review, unless other circumstances occur.

In certain embodiments, the threshold normal confidence level may be adjusted to make the algorithm more specific or more sensitive to classifying ECG recordings 10 in the normal group 26 that bypasses clinician review. For example, the normal detection model 25 may have a sensitivity/specificity mode setting where the threshold normal confidence level is adjusted accordingly. For example, in a high specificity mode the algorithm may have a high specificity for detecting normal ECG rhythms that can bypass clinician review, thereby increasing the requirement for categorization into the normal group 26—e.g. the threshold normal confidence level is set to a higher value. Conversely, the sensitivity of the bypass determination may be increased in order to capture a greater number of the normal ECG recordings 10 that will bypass clinician review by having a high sensitivity mode—e.g., where the threshold normal confidence level is set to a lower value. Similarly, other modes may be provided between the high sensitivity mode and the high specificity mode, such as a balanced mode where the threshold confidence level is set to a value in between that for the high sensitivity mode and the high specificity mode.

Figure 5:
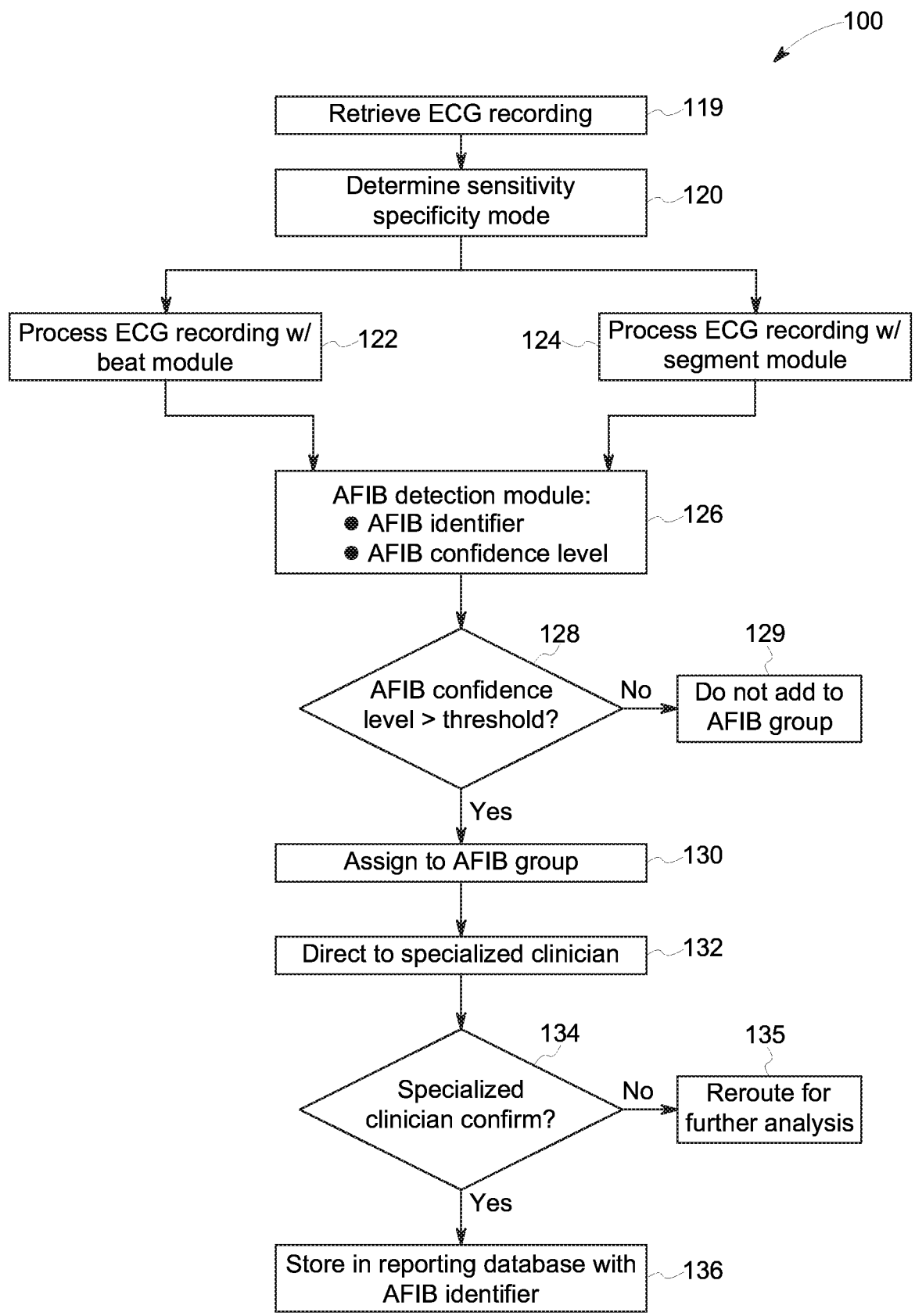

FIG. 5 depicts another embodiment of a method 100 of processing a group of ECG wave forms from multiple patients, and specifically a portion thereof relating to abnormality detection. In the specific example exemplified at FIG. 5, the steps are directed to detection of atrial fibrillation, which provides just one example of the various abnormalities that the abnormality detection module 23 may be configured to detect. At step 119 an ECG recording 10 is retrieved, such as an ECG recording that is not removed by the noise analytic module 21. Alternatively, the ECG recording 10 may be retrieved directly from the pre-processing database 11. A sensitivity/specificity mode is determined at step 120. Such mode may be determined based on user input or based on other variables known to the system. One example of such a mode determination is provided and described below with respect to FIG. 6. For example, a mode may be selected between a high sensitivity mode, a high specificity mode, and a balanced mode. The specificity/sensitivity mode selection dictates the operation of the abnormality detection, and may affect various determinations or thresholds, examples of which are described at various locations herein.

The ECG recording 10 is then processed with both a beat module 312, at step 122, and a segment module 314, at step 124. As described in further detail below, the beat module 312 conducts a beat-by-beat analysis of a time series of ECG data to detect AFIB based on rhythm variability, such as variation in the RR interval, and the segment module 314 breaks the time series of ECG data into time segments of data, which may be overlapping time segments, and analyzes the time segments to determine whether AFIB is present or absent based on eliminating the probability of other rhythms and arrhythmia types. Thereby, the depicted AFIB detection method uses two different ECG processing methods in parallel to process the ECG data. The results of the beat module 312 and the segment module 14 are then compared at step 112 to determine an AFIB identifier indicating the presence or absence of AFIB in the relevant section of ECG data, and in the overall ECG recording 10. For example, the output of the beat module 312 and the segment module 314 may be assessed by an AFIB detection module that executes varying logic to compare the outputs, such as based on the sensitivity/specificity mode.

The AFIB detection module 316 may be further configured to determine an AFIB confidence level (which is one example of an abnormality confidence level) 38 representing the confidence of the presence of AFIB in the ECG recording 10, or respective portion thereof. For example, the AFIB confidence level 38 may be determined as a running value based on all previous AFIB identification values 36 for the respective ECG recording 10.

In certain embodiments, the AFIB confidence level 38 may be decreased when significant noise is present in the ECG recording 10. For example, when the noise level exceeds a noise level threshold, the confidence level may be reduced by a predetermined amount. To provide just one example, the AFIB confidence level 38 may be reduced by 20% upon detection of at least the threshold noise. In such embodiments, the noise level detection may be accounted for without providing a separate noise analytic module 21 or preprocessing to divide out the noise group 22.

Once all of the respective ECG recording 10 has been processed by the AFIB detection module 316, and one or more AFIB identifiers 36 and an AFIB confidence level 38 have been determined for the respective ECG recording, then step 128 is executed to determine whether the AFIB confidence level 38 exceeds a confidence level threshold. As described above with respect to the normal confidence level threshold, the AFIB confidence level threshold may be increased or decreased based on the selected sensitivity/ specificity mode. If the AFIB confidence level 38 is not greater than the threshold, then the ECG recording is not classified into the AFIB group at step 129. In certain embodiments, assessment may continue for detection of other abnormalities, or if no abnormality is detected by the abnormality detection module 23, then the ECG recording 10 may be assessed by the normal detection module 25 as described above.

If the AFIB confidence level 38 does exceed the threshold, then the respective ECG recording 10 is assigned to the AFIB group at step 130. The ECG recordings 10 assigned to the AFIB group are then reviewed by a respective specialized clinician 28a-28n at step 132, where the specialized clinician 28 is sufficiently trained and certified for competent detection of AFIB in ECG wave forms. Moreover, the AFIB identifier 36 and AFIB confidence level 38 can provide additional information, over and above the ECG data, which can be used by the specialized clinician 28 to assess the ECG recording 10. The specialized clinician 28 either confirms or rejects the AFIB identification generated by the abnormality detection module 23, and provides input accordingly. At step 134, if the specialized clinician has confirmed the AFIB detection, then the respective ECG recording 10 is stored in the reporting database 15 with the AFIB identifier, represented at step 136. If the specialized clinician does not confirm, and instead rejects the AFIB identification, then the ECG recording 10 is rerouted for further analysis at step 135. For example, the specialized clinician may route the ECG recording to a different specialized clinician 28a-28n for review, or may provide a different abnormality identifier 36 and may store that abnormality identifier in the reporting database 15 with the ECG recording 10.

Figure 6:
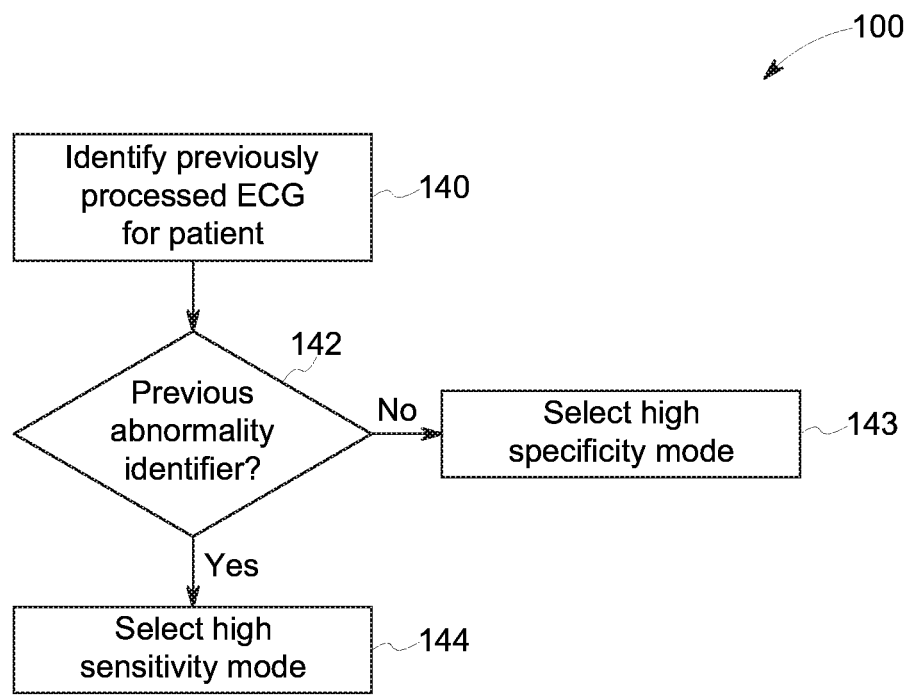

FIG. 6 depicts one embodiment of a method 100 portion for determining the sensitivity/specificity mode, which in the depicted embodiment is determined based on previous abnormality identifiers for the patient. The previously processed ECG's for the particular patient associated with the currently-assessed ECG recording 10. If a previous abnormality identifier is associated with one of those previously-processed ECG recordings for the particular patient, as determined at step 142, then the high sensitivity mode is selected at step 144. In certain embodiments, the high sensitivity mode may be selected for certain abnormality detection algorithms based on the previous abnormality identifier(s). If no previous abnormality identifier is detected at step 142, then the high specificity mode is selected at step 143.

FIG. 5 depicts one embodiment of a method 100 of processing ECG recordings 10 to detect AFIB Likewise, the AFIB detection steps depicted in FIG. 5 provide just one example of abnormality detection, including determination of an abnormality identifier 36 and an abnormality confidence level 38, which in other embodiments would represent other abnormalities determined according to differing logic.

Figure 8:
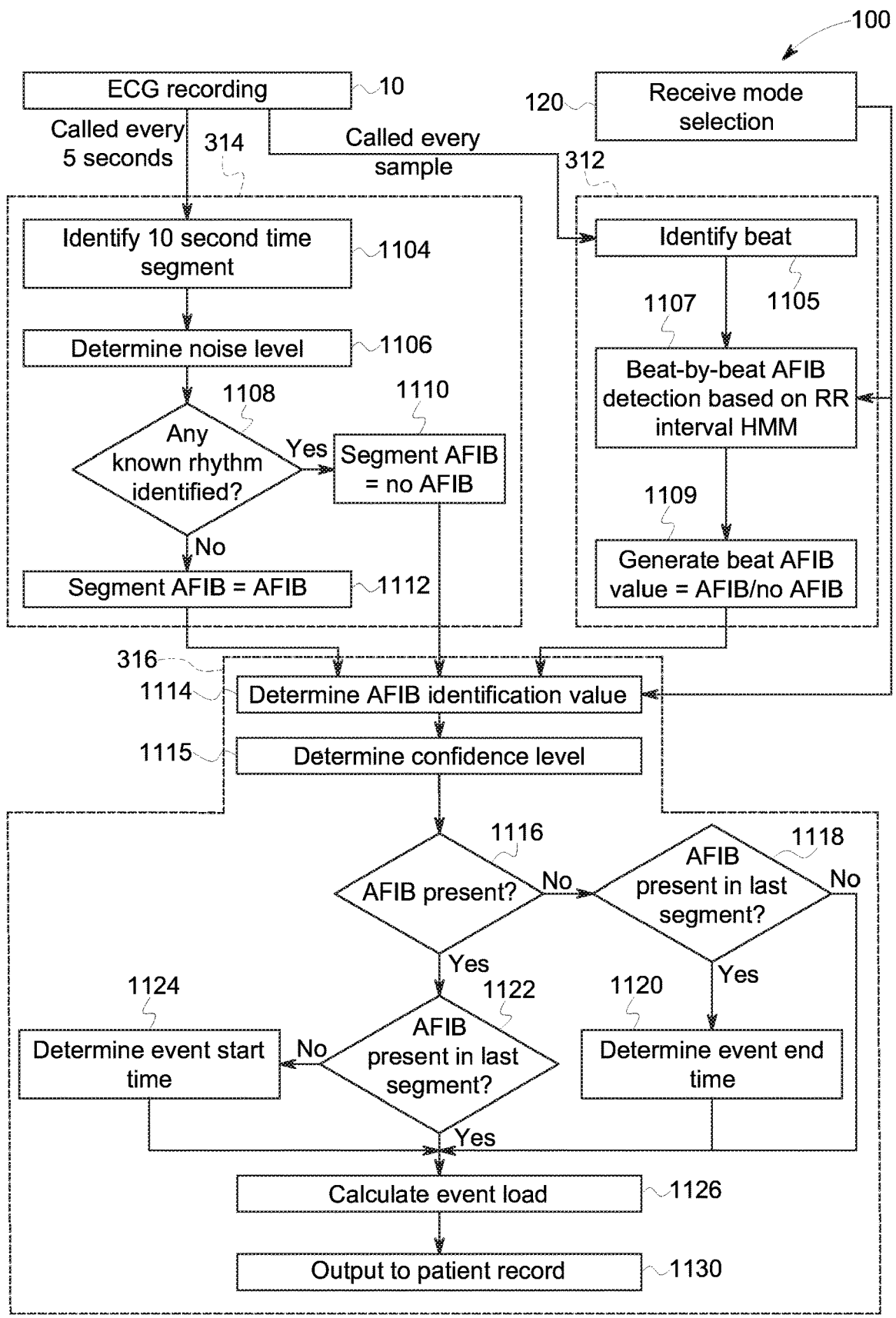
FIG. 8 is a flowchart representing one embodiment of a method of processing ECG data to detect atrial fibrillation.

FIGS. 7-8 provide further exemplification of AFIB detection that could be implemented, such as in the method shown and described at FIG. 5. In the example at FIG. 8, the sample points of the time series of ECG data from the ECG recording 10 are continually received and processed in parallel by the beat module 312 and segment module 314. The time series of ECG data is thus processed by both modules, which utilize differing analysis methods to determine whether AFIB is present throughout the time series of ECG data. The results of the beat module 312 and the segment module 314 are then compared to generate an AFIB identifier 36 indicating the presence or absence of AFIB in the relevant section of ECG data. If results of both approaches agree, namely the output of each of the beat module 312 and the segment module 314 provide the same determination regarding the presence or absence of AFIB, then the result is more likely to be correct.

The beat module 312 determines a beat AFIB value based on a timing of each identified heartbeat in the time series of ECG recordings 10, wherein the beat AFIB value represents a presence or absence of AFIB based on variability in the timing of each identified heartbeat. In one embodiment, the beat AFIB module 312 utilizes a Hidden Markov Model (HMM) to continually process the time series of ECG data and statistically assess whether AFIB is present. In one embodiment, the HMM is configured to represent the RR intervals, such as with respect to a sliding average RR interval, in one of two states: chaotic or organized, or AFIB or NO AFIB, respectively. For example, the HMM may be trained using a database of ECG data selected to contain AFIB, normal sinus rhythm, and other rhythms considered likely to be confused with AFIB. For each beat, the current score of HMM value is updated. Then a buffer containing previous history of HMM score is also updated. The average HMM score is calculated for every updating cycle, which is the beat AFIB value. The timing of the beat AFIB value calculation may correspond with the output of the segment module 314 so that the values can be accurately compared to determine the AFIB identifier 36. For example, the beat AFIB value may be outputted every five seconds, and the segment module 314 may analyze time segments that shift by five seconds, such as overlapping time segments having a start time that shifts by five seconds.

In one embodiment, the segment module 314 is operated to perform a running mode analysis of overlapping segments of the ECG recordings 10 to produce a segment AFIB value for each overlapping segment of the ECG recordings 10. For example, the segment module 314 may comprise software instructions executable to identify whether any rhythm from a set of known rhythms, which may include various arrhythmia patterns, are likely to be present in the time segment of ECG recordings 10, in which case it would rule out the presence of AFIB. To provide just a few examples, the set of known rhythms (which include known arrhythmia patterns) may include any one or more of the following: the presence of P-waves, artificial pacing, ectopic atrial rhythm, atrial flutter, junctional rhythm, or PACs. For example, if the presence of P waves or PACs are detected, then the presence of AFIB in the time segment may be ruled out.

The segment module 314 divides the time series of ECG recordings 10 into consecutive time segments, which may be overlapping time segments. The ECG data in each of the time segments has been analyzed to determine a segment AFIB value for that time segment, wherein the segment AFIB value indicates a presence or absence of AFIB in the time segment based on whether any of the set of known rhythms are identified. For example, the time segments may be ten second segments of the ECG recordings 10. In one embodiment, the segment module 314 may overlap the time segments such that each sample in the ECG recordings 10 is analyzed as part of at least two time segments. For example, the segment module 314 may be configured to shift the time segments in five second increments. In an embodiment where the time segments are ten seconds long, each data point, or sample, will be analyzed as part of two time segments. This provides a robust data analysis.

In certain embodiments, the AFIB detection methods and logic executed by the segment module 314 may have some hysteresis effect where once a normal sinus rhythm (NSR) is detected the segment AFIB value may rule out the presence of AFIB for a number of time segments. For example, as seen in FIG. 7, once a normal sinus rhythm is detected the segment AFIB value remains at 0 for two five second intervals following detection of the normal sinus rhythm. Thus, once a normal sinus rhythm is detected, it takes a few analysis intervals for the segment AFIB value to flip back to AFIB as the running answer.

The system 1 further includes an AFIB detection module 316 that determines an AFIB identifier 36 based on the beat AFIB value and the segment AFIB value. If both the beat AFIB value and the segment AFIB value indicate the presence of AFIB, then the AFIB identifier 36 will also indicate the presence of AFIB. If the beat AFIB value and the segment AFIB value both indicate an absence of AFIB, then the AFIB identifier 36 will be zero or otherwise indicate an absence of AFIB. In the case situation where the beat AFIB value and the segment AFIB value do not agree, the AFIB detection module 36 may be operable in various modes to execute differing logic for handling disagreements between the beat AFIB value and the segment AFIB value. For example, the AFIB detection module may be configured to operate in one of three modes, including a high sensitivity mode, a high specificity mode, and a balanced mode to determine the AFIB identifier 36 based on the beat AFIB value and the segment AFIB value.

FIG. 7 depicts an exemplary embodiment of the logic executed in three different modes to determine the AFIB identifier 36. In the explanatory example, each of the beat module 312 and the segment module 314 output respective values indicating the presence or absence of AFIB (either a 1 or a 0, respectively) for every five second increment of ECG recordings 10. The example shows five such values; however, it should be understood that the values will continue for the length of the time sequence of ECG recordings 10.

In the example, the AFIB detection module 316 can operate in the high sensitivity mode where the AFIB identifier 36 indicates a presence of AFIB when either the beat AFIB value or the segment AFIB value indicates the presence of AFIB. Thus, in high sensitivity mode, an OR Boolean operator is used to compare the beat AFIB value and the segment AFIB value. Further, in high sensitivity mode the threshold for the HMM to recognize an organized RR pattern may be increased. This increases the chance that the beat module 312 will detect that the ECG recordings 10 is chaotic and generate a beat AFIB value indicating the presence of AFIB, thus increasing the sensitivity of the AFIB detection by the beat module 312. Alternatively, the AFIB detection module 316 may operate in a high specificity mode where the AFIB identifier 36 indicates a presence of AFIB when both of the beat AFIB value and the segment AFIB value indicate the presence of AFIB. Thus, in high specificity mode an AND Boolean operator is used to compare the beat AFIB value with the segment AFIB value. The AFIB detection module 316 may be further operable in a balanced mode where the AFIB identifier 36 indicates a presence of AFIB when either the beat AFIB value or the segment AFIB value indicates the presence of AFIB. In certain embodiments, the beat module 312 has a lower threshold for detecting the presence of AFIB in the high sensitivity mode than in the balanced mode, thus the sensitivity of the detection algorithm will be greater in the sensitivity mode than in the balanced mode.

In certain embodiments, the operating mode may be selected by a user. For example, the user may select one of the high sensitivity mode, the high specificity mode, or the balanced mode via the user interface associated with the system 1. In other embodiments, the operating mode may be automatically determined based on certain factors, such as based on the ECG history for the respective patient (e.g., exemplified at FIG. 6).

In certain embodiments, a confidence level (CL) may be calculated for each AFIB identifier. For example, the confidence level may be a running value accounting for all AFIB identifier 36 determined for the time series of ECG recordings 10. For example, the confidence level (CL) may be determined as the total number of AFIB identifier 36 indicating the presence of AFIB (e.g., equal to 1) divided by the total number of AFIB identifier 36 overall. The confidence level may be expressed as a percentage—e.g., the percent of AFIB identifier 36 indicating the presence of AFIB. Thus, depending on the mode being executed by the AFIB detection module 316, the confidence level may vary. Referring to the example of FIG. 7, CL would equal 100% for the first time segment, 50% for the second time segment, and CL would vary for the remaining time segments depending on the mode of operation executed by the AFIB detection module 316.

In certain embodiments, the confidence level may also account for a noise level of the respective segment of ECG data analyzed. The noise level may be assessed by logic incorporated in either the beat module 312, the segment module 314, or by a separate noise analytic module 21 as described above. In the depicted embodiment, the segment module 314 measures the noise level in the analyzed segment of the time series of ECG recordings 10 and generates a positive value if the noise exceeds a noise threshold and a negative value (or a 0) if the noise level does not exceed the noise threshold. In other embodiments, the noise level may be placed on a noise scale, or may otherwise by indicated by using more than two values. The confidence level may then be decreased when significant noise is present in the time segment. For example, when the noise level exceeds a noise level threshold, the confidence level may be reduced by a predetermined amount. In the depicted example, the noise level determined by the segment module 314 exceeds the noise level threshold for one time segment, and the confidence level (CL) is reduced by 20% by the AFIB detection module 316 for the corresponding time segment. In other embodiments where the noise level determination may include more than two values, the confidence level may be reduced by an increasing percentage amount for increasing noise levels.

Returning to FIG. 3, with respect to the beat module 312, instructions are executed to analyze the ECG recordings 10 on a sample-by-sample basis to identify beats at step 1105 within the ECG recordings 10. Upon identification of a beat, the HMM determines at step 1107 whether the beats represents a chaotic or an organized RR interval, which is a determination made based on all of the ECG recordings 10 processed thus far by the beat module 312. The threshold used by the HMM for determining whether the beat data is organized or chaotic may be adjusted based on the mode selection 30 by a user, which is received at step 1102. As described above, the mode selection 30 may adjust the sensitivity of the AFIB detection by the HMM. The state of the HMM AFIB determination is polled at a regular interval, such as every five seconds, to generate the beat AFIB value at step 1109. The period at which the beat AFIB value is polled, or generated, may be shorter or longer than five seconds, as it may correspond to the length of the segments, or segment shifts, executed by the segment module 314. In other embodiments, such as that depicted at FIG. 6, the mode selection 30 may be automatically generated within the system 1, such as based on assessment of previous abnormality identifiers.

The segment module 314 operates on the ECG recordings 10 in parallel with beat module 312. The segment module 314 calls the ECG recordings 10 in time segments. In the depicted embodiment, the segment module 314 calls new data every five seconds and analyzes a shifting ten second time segment, identified at step 1104. The noise level of the ECG data in the time segment is determined at step 1106. For example, the signal-to-noise ratio may be determined and classified, such as by comparing it to one or more noise level thresholds. Instructions are executed at step 1108 to determine whether any known rhythm can be identified, such as the presence of a P wave, a normal sinus rhythm (NSR), artificial pacing, ectopic atrial rhythm, atrial flutter, junctional rhythm, or premature atrial contractions (PACs). If any such known rhythm is identified, then the segment module 314 determines that AFIB is not present and assigns the segment AFIB value to indicate no AFIB (such as equaling 0). If no known rhythm is identified, then the presence of AFIB is positively determined for the time segment and the segment AFIB value is set at step 1112 to indicate the presence of AFIB (such as equaling one). Logic is then executed at step 1114, such as by executing code embodied in the AFIB detection module 316, to determine the AFIB identifier 36 based on the beat AFIB value and segment AFIB value. The AFIB detection module 316 may execute varying logic depending on the user mode selection 30 received at step 1102, such as whether the system is operating in high sensitivity mode, high specificity mode, or balanced mode. The AFIB detection module 316 may further determine the confidence level 38 for the respective time segment, which may be a running value based on all previous AFIB identifiers 36 for the time series of ECG.

The AFIB detection module 316 may then analyze the AFIB identifier 36 over time, such as to present information aggregating the AFIB identifier 36 for the ECG recording 10. For example, the AFIB identifier 36 may be analyzed to identify continuous AFIB events within the ECG recordings 10 and calculate an event load 44. In certain embodiments, the AFIB analysis logic may be called once all of the AFIB identifiers 36 have been determined for the time series of ECG recordings 10. If a received AFIB identifier 36 indicates that AFIB is not present, as determined at step 1115, then logic is executed to determine whether AFIB was present in the last segment, which is represented at box 1118. If AFIB was present in the last time segment, but is not currently present, then an AFIB event has ended, and an event end time is determined at step 1120 for the AFIB event. If the received AFIB identifier 36 did indicate the presence of AFIB, as determined at step 116, then logic is executed at step 1122 to determine whether AFIB was present in the last segment. If AFIB was not previously present, but now is, then an event start time is determined at step 1124. If AFIB was present in the last segment and continues to be present, then the AFIB event continues through the current segment. A running event load value may be calculated at step 1126 based on the available event start times and end time. For example, the event load may represent a total percent of time segments processed thus far where AFIB was detected, thus representing the percentage of the time series of ECG recordings 10 where AFIB is determined to be present. Alternatively or additionally, the event load may account for a number of separate AFIB events (each having a start and an end time), and thus may indicate whether AFIB was continuously detected for long periods or whether it was detected in short bursts, separated by intermittent detection of organized and/or known rhythms.

Figure 3:
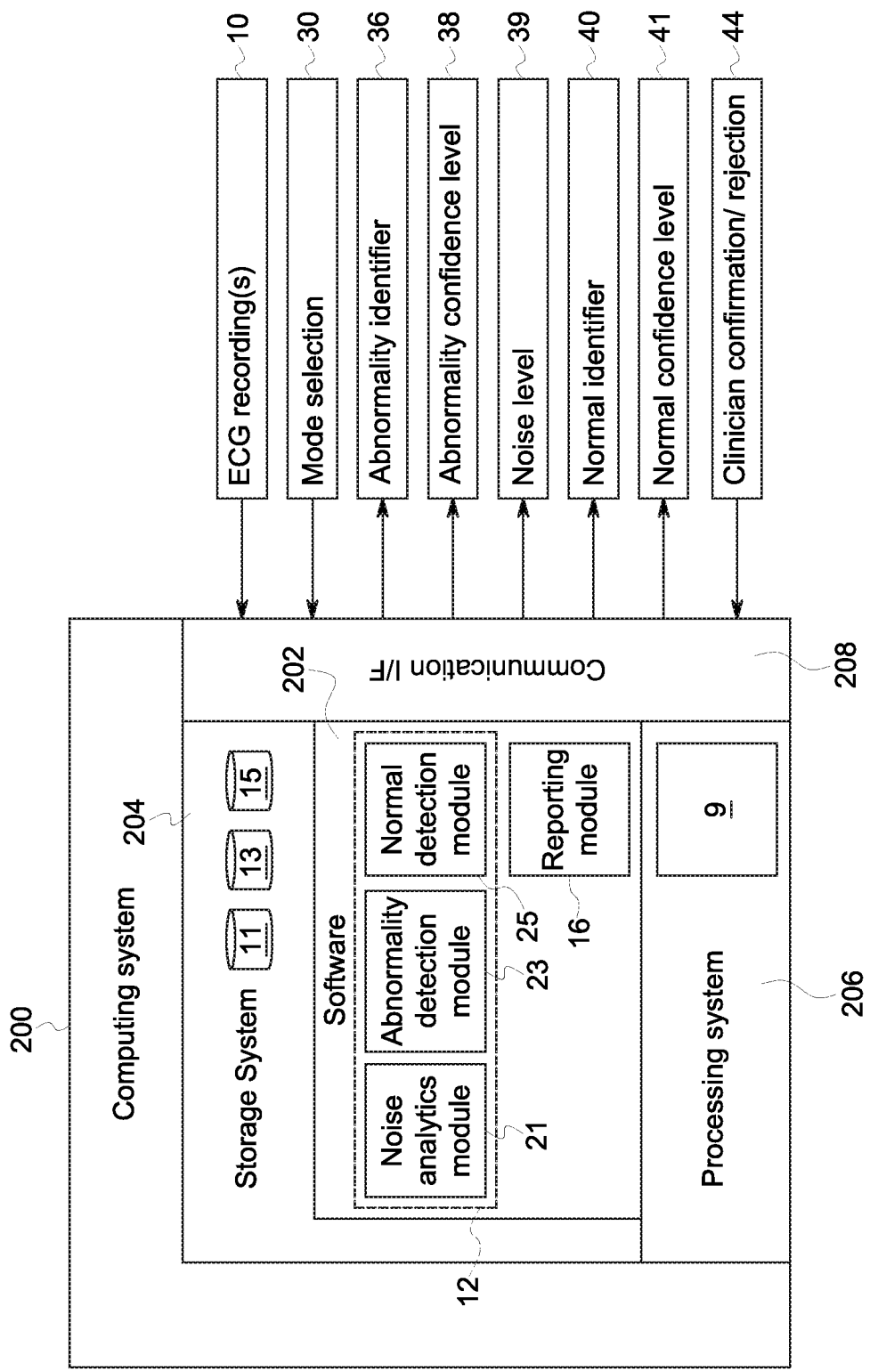
FIG. 3 is a schematic diagram of a computing system that incorporated in one embodiment of a system for processing ECG recordings from multiple patients.

FIG. 3 provides system diagram computing system 200 for the central processing facility. The computing system 200 includes a processing system 206, storage system 204, software 202, and communication interface 208. The processing system 206 loads and executes software 202 from the storage system 204, including the triage module 12 (and/or sub-modules 21, 23, 25) and the reporting module 16, which are applications within the software 202. Each of the modules 12, 16, 21, 23, 25, 321, 314, 316 includes computer-readable instructions that, when executed by the computing system 200 (including the processing system 206), direct the processing system 206 to operate as described in herein in further detail.

Although the computing system 200 as depicted in FIG. 3 includes one software 202 encapsulating the aforementioned modules, it should be understood that one or more software elements having one or more modules may provide the same operation. Similarly, while description as provided herein refers to a computing system 200 and a processing system 206, it is to be recognized that implementations of such systems can be performed using one or more processors, which may be communicatively connected, and such implementations are considered to be within the scope of the description.

The processing system 206 includes the processor 9, which may be a microprocessor, a general purpose central processing unit, an application-specific processor, a microcontroller, or any other type of logic-based device. The processing system 206 may also include circuitry that retrieves and executes software 202 from storage system 204. Processing system 206 can be implemented within a single processing device but can also be distributed across multiple processing devices or sub-systems that cooperate in executing program instructions.

The storage system 204, which includes the pre-processing database 11, abnormality database(s) 13, and reporting database 15, can comprise any storage media, or group of storage media, readable by processing system 206, and capable of storing software 202. The storage system 204 can include volatile and non-volatile, removable and non-removable media implemented in any method or technology for storage of information, such as computer-readable instructions, data structures, program modules, or other data. Storage system 204 can be implemented as a single storage device but may also be implemented across multiple storage devices or sub-systems. For example, the software 202 may be stored on a separate storage device than the databases 11, 13, 15. Likewise, each database 11, 13, 15 can be stored, distributed, and/or implemented across one or more storage media or group of storage medias. Similarly, each database 11, 13, 15 may encompass multiple different sub-databases at different storage locations and/or containing different information which may be stored in different formats. Storage system 204 can further include additional elements, such a controller capable of communicating with the processing system 206.

Examples of storage media include any types of memory or storage device, or any other medium which can be used to store the desired information and that may be accessed by an instruction execution system, as well as any combination or variation thereof, or any other type of storage medium. Likewise, the storage media may be housed locally with the processing system 206, or may be distributed in one or more servers, which may be at multiple locations and networked, such as in cloud computing applications and systems. In some implementations, the storage media can be a non-transitory storage media. In some implementations, at least a portion of the storage media may be transitory.

The communication interface 208 interfaces between the elements within the computing system 200 and external devices, such as a user interface and/or data reception devices to receive the multitude of ECG recordings 10 from the central monitoring system 8 or the ECG monitors 5.

Returning to FIG. 1 the reporting module 16 generates an ECG report 18 for each patient comprising all of the processed ECG recordings 10 for that patient, along with any abnormality identifiers 36 abnormality confidence levels 38, normal identifiers 40, and normal confidence levels 41. Thereby, the ECG recordings for the patient are included, which may include ECG recordings 10 from both the normal group 26 and/or one or more abnormality groups 24. Such reports 18 may then be reviewed by the ordering physician and/or stored in the patient's medical record.

This written description uses examples to disclose the invention, including the best mode, and also to enable any person skilled in the art to make and use the invention. Certain terms have been used for brevity, clarity and understanding. No unnecessary limitations are to be inferred therefrom beyond the requirement of the prior art because such terms are used for descriptive purposes only and are intended to be broadly construed. The patentable scope of the invention is defined by the claims, and may include other examples that occur to those skilled in the art. Such other examples are intended to be within the scope of the claims if they have features or structural elements that do not differ from the literal language of the claims, or if they include equivalent features or structural elements with insubstantial differences from the literal languages of the claims.

The invention claimed is:

1. A system for processing ECG recordings from multiple patients, the system comprising:
   a pre-processing database containing unprocessed ECG recordings from multiple patients, wherein each ECG recording is a time series of ECG data recorded from a patient;
   a reporting database containing processed ECG recordings from multiple patients;
   a processor;
   a triage module executable on the processor to:
      assess each of the unprocessed ECG recordings from the multiple patients in the pre-processing database to detect a presence or absence of at least one known abnormality and determines at least one abnormality identifier based on the detected known abnormality;
      identify at least one abnormality group of ECG recordings from multiple patients based on the abnormality identifier;
      identify a normal group of ECG recordings from multiple patients that are not in the abnormality group; and
      store the normal group of ECG recordings in the reporting database with an associated normal identifier.

2. The system of claim 1, wherein the triage module is further executable to:
   provide each abnormality group of ECG recordings from multiple patients for specialized clinician review based on the abnormality identifiers;
   receive confirmation or rejection of each the abnormality identifier from the specialized clinician; and
   for the ECG recordings in the abnormality group where the abnormality identifier is confirmed, storing each respective ECG recording in the reporting database in association with the confirmed abnormality identifier.

3. The system of claim 2, further comprising a reporting module executable on the processor to generate an ECG report for each of the multiple of patients containing all ECG recordings for the respective patient from the normal group and the normal identifier and all ECG recordings for the respective patient from the abnormal group and the confirmed abnormality identifier.

4. The system of claim 1, wherein the triage module is further executable to determine an abnormality confidence level representing the likelihood of the presence or absence of the known abnormality, wherein each abnormality group is comprised of ECG recordings having the same abnormality identifiers with abnormality confidence levels greater than a threshold abnormality confidence level.

5. The system of claim 4, wherein the triage module is further executable to determine a noise level for each ECG recording, wherein the abnormality confidence level is determined based further on the noise level.

6. The system of claim 4, wherein the triage module is further executable to:
   receive a mode selection between at least a high sensitivity mode and a high specificity mode;
   determine the threshold abnormality confidence level based on the mode selection, wherein the threshold abnormality confidence level is lower in the high specificity mode than in the high sensitivity mode.

7. The system of claim 1, wherein the triage module is further executable to:
   direct each abnormality group of ECG recordings from multiple patients for specialized clinician review based on the abnormality identifier.

8. The system of claim 7, wherein the abnormality group is an atrial fibrillation (AFIB) group consisting of ECG recordings with an abnormality identifier indicating a threshold AFIB confidence level of the presence of AFIB in the ECG waveform; and
   wherein the specialized clinician is trained to identify AFIB in ECG waveforms;
   wherein the triage module is further executable to:
      provide the specialized clinician with the AFIB confidence level; and
      receive one of a confirmation confirming the presence of AFIB in the ECG recording or a rejection indicating that AFIB is not present in the ECG recording.

9. The system of claim 1, wherein identifying the normal group of ECG recordings includes assessing each ECG recording to detected a sinus rhythm in the respective ECG recording, and wherein the triage module is further executable to:
   determine a normal confidence level for each of the ECG recordings in the normal group, wherein the normal confidence level represents the likelihood that a normal sinus rhythm is dominant in the respective ECG recording;
   store ECG recordings having at least a threshold normal confidence level in a reporting database; and
   direct ECG recordings having less than the threshold normal confidence level for clinician review.

10. The system of claim 1, wherein the triage module is further executable to:
    locate one or more previously processed ECG recordings from a respective one of the multiple patients within the reporting database;

determine whether any of the previously processed ECG recordings from the respective patient are associated with a previous abnormality identifier;

if the previous abnormality identifier is detected for the respective patient, selecting a high sensitivity mode for abnormality grouping; and if the previous abnormality identifier is not detected for the respective patient, selecting a high specificity mode for abnormality grouping.

11. A method of processing ECG recordings from multiple patients, the method comprising:

receiving a batch of ECG recordings from multiple patients, wherein each ECG recording is a time series of ECG data recorded from a patient;

assessing the ECG recordings in the batch to detect a presence or absence of at least one known abnormality in the respective ECG recording;

for each ECG recording where a known abnormality is detected, determining at least one abnormality identifier based on the detected known abnormality;

identifying one or more abnormality groups within the batch of ECG recordings based on the abnormality identifiers, wherein each abnormality group includes ECG recordings from multiple patients;

identifying a normal group of ECG recordings within the batch of ECG recordings that are not in the one or more abnormality groups, wherein the normal group includes ECG recordings from multiple patients; and storing a normal identifier in association with each ECG recording in the normal group of ECG recordings.

12. The method of claim 11, further comprising:

storing the normal group of ECG recordings in a reporting database;

providing each abnormality group of ECG recordings for specialized clinician review based on the abnormality identifier;

receiving confirmation or rejection of the abnormality identifier from the specialized clinician; and for the ECG recordings in the abnormality group where the abnormality identifier is confirmed, storing each respective ECG recording in the reporting database in association with the confirmed abnormality identifier.

13. The method of claim 12, generating an ECG report for each of the multiple of patients containing all ECG recordings for the respective patient from the normal group and the normal identifier and all ECG recordings for the respective patient from the abnormal group and the confirmed abnormality identifier.

14. The method of claim 11, wherein determining the abnormality identifier includes determining an abnormality confidence level representing the likelihood of the presence or absence of the known abnormality; and wherein determining the abnormality group includes comparing the abnormality confidence level to a threshold such that each abnormality group is comprised of ECG recordings having the same abnormality identifiers with confidence levels greater than a threshold abnormality confidence level.

15. The method of claim 14, further comprising determining a noise level for each ECG recording, wherein the abnormality confidence level is determined based further on the noise level.

16. The method of claim 14, further comprising:

receiving a mode selection between at least a high sensitivity mode and a high specificity mode;

determining the threshold abnormality confidence level based on the mode selection, wherein the threshold abnormal confidence level is lower in the high specificity mode than in the high sensitivity mode.

17. The method of claim 11, further comprising determining further comprising:

determining a noise level for each ECG recording;

comparing the noise level to a threshold noise level to identify a noise group as ECG recordings within the batch; and wherein the noise group of ECG recordings are removed from the batch such that they are not included in the normal group or the one or more abnormality groups.

18. The method of claim 17, wherein the abnormality group is an atrial fibrillation (AFIB) group consisting of ECG recordings with an abnormality identifier indicating a threshold AFIB confidence level of the presence of AFIB in the ECG waveform; and wherein the specialized clinician is trained to identify AFIB in ECG waveforms;

further comprising providing the specialized clinician with the AFIB confidence level; and receiving one of a confirmation confirming the presence of AFIB in the ECG waveform or a rejection indicating that AFIB is not present in the ECG waveform.

19. The method of claim 11, wherein identifying the normal group of ECG recordings includes assessing each ECG recording to detect a sinus rhythm in the respective ECG recording, and further comprising:

determining a normal confidence level for each of the ECG recordings in the normal group, wherein the normal confidence level represents the likelihood that a normal sinus rhythm is dominant in the respective ECG recording;

storing ECG recordings having at least a threshold normal confidence level in a reporting database; and directing ECG recordings having less than the threshold normal confidence level for clinician review.

20. The method of claim 11, further comprising, prior to determining the abnormality identifier:

locating one or more previously processed ECG recordings from the patient within a database of processed ECG recordings;

determining whether any of the previously processed ECG recordings from the patient are associated with a previous abnormality identifier;

if the previous abnormality identifier is detected, selecting a high sensitivity mode for abnormality grouping; and if the previous abnormality identifier is not detected, selecting a high specificity mode for abnormality grouping.

* * * * *